United States Patent
Jackson et al.

(10) Patent No.: US 11,617,785 B2
(45) Date of Patent: Apr. 4, 2023

(54) TREATMENT OF INFLAMMATORY SKIN DISORDERS

(71) Applicant: ZZ Biotech LLC, Houston, TX (US)

(72) Inventors: Christopher John Jackson, Mt. Colah (AU); Meilang Xue, Campsie (AU)

(73) Assignee: ZZ Biotech LLC, Houston, TX (US)

( * ) Notice: Subject to any disclaimer, the term of this patent is extended or adjusted under 35 U.S.C. 154(b) by 195 days.

(21) Appl. No.: 16/880,243

(22) Filed: May 21, 2020

(65) Prior Publication Data

US 2020/0276281 A1    Sep. 3, 2020

Related U.S. Application Data

(60) Division of application No. 15/365,567, filed on Nov. 30, 2016, now abandoned, which is a continuation of application No. 14/409,215, filed as application No. PCT/AU2013/000729 on Jul. 4, 2013, now abandoned.

(30) Foreign Application Priority Data

Jul. 4, 2012    (AU) .............................. 2012902874

(51) Int. Cl.
  *A61K 38/48*    (2006.01)
  *A61K 9/06*    (2006.01)
  *A61K 45/06*    (2006.01)
  *A61K 9/00*    (2006.01)

(52) U.S. Cl.
  CPC ........ *A61K 38/4866* (2013.01); *A61K 9/0019* (2013.01); *A61K 9/06* (2013.01); *A61K 45/06* (2013.01); *C12Y 304/21069* (2013.01)

(58) Field of Classification Search
  CPC .... A61K 9/0019; A61K 9/06; A61K 38/4866; A61K 45/06; A61P 17/06; A61P 17/02; A61P 37/00; A61P 17/10; A61P 17/00; A61P 37/06; A61P 37/08; C12Y 304/21069
  See application file for complete search history.

(56) References Cited

U.S. PATENT DOCUMENTS

| | | |
|---|---|---|
| 4,775,624 A | 10/1988 | Bang et al. |
| 4,959,318 A | 9/1990 | Foster et al. |
| 4,981,952 A | 1/1991 | Yan |
| 5,084,274 A | 1/1992 | Griffin et al. |
| 5,093,117 A | 3/1992 | Lawrence et al. |
| 5,151,268 A | 9/1992 | Bang et al. |

(Continued)

FOREIGN PATENT DOCUMENTS

| | | |
|---|---|---|
| AU | 658881 | 11/1992 |
| CA | 2041380 C | 10/1997 |

(Continued)

OTHER PUBLICATIONS

Branisteanu et al, Experimental and Therapeutic Medicine, 2022, 23:201, 13 pages (Year: 2022).*

(Continued)

*Primary Examiner* — Jana A Hines
(74) *Attorney, Agent, or Firm* — Myers Bigel, P.A.

(57) ABSTRACT

The invention relates to methods of using an effective amount of activated protein C (APC) to treat an individual for a skin disorder characterised by the presence of hyperproliferative keratinocytes.

21 Claims, 3 Drawing Sheets

(56) References Cited

U.S. PATENT DOCUMENTS

| | | | |
|---|---|---|---|
| 5,453,373 | A | 9/1995 | Gerlitz et al. |
| 5,516,650 | A | 5/1996 | Foster et al. |
| 5,571,786 | A | 11/1996 | Eibl et al. |
| 5,726,205 | A | 3/1998 | Woitun et al. |
| 5,831,025 | A | 11/1998 | Ogata et al. |
| 6,037,322 | A | 3/2000 | Grinnell et al. |
| 6,156,734 | A | 12/2000 | Grinnell et al. |
| 6,159,468 | A | 12/2000 | Carlson |
| 6,268,344 | B1 | 7/2001 | Grinnell et al. |
| 6,395,270 | B1 | 5/2002 | Carlson et al. |
| 8,728,512 | B2 | 5/2014 | Jackson et al. |
| 8,912,142 | B2 * | 12/2014 | Sprecher ............... A61P 37/08 514/8.7 |
| 2007/0224150 | A1 | 9/2007 | Chung |
| 2008/0293631 | A1 * | 11/2008 | Jackson et al. ........... A61P 3/10 514/44 R |
| 2011/0129546 | A1 | 6/2011 | Umbert Mill |
| 2012/0022254 | A1 * | 1/2012 | Nunes ................... A61P 13/02 544/119 |
| 2015/0150954 | A1 * | 6/2015 | Jackson ................ A61K 45/06 424/94.64 |
| 2017/0042982 | A1 * | 2/2017 | Jackson ................ A61P 17/00 |
| 2017/0080062 | A1 * | 3/2017 | Jackson ................ A61K 45/06 |
| 2018/0243383 | A1 * | 8/2018 | Xue .................... A61K 38/4866 |
| 2019/0060421 | A1 * | 2/2019 | Jackson ................ A61P 17/00 |
| 2020/0000890 | A1 * | 1/2020 | Xue ................... A61P 17/02 |
| 2020/0108128 | A1 * | 4/2020 | Jackson ............. A61K 38/4866 |
| 2020/0276281 | A1 * | 9/2020 | Jackson ............... A61K 9/0019 |
| 2021/0268062 | A1 * | 9/2021 | Jackson ................ A61P 17/00 |

FOREIGN PATENT DOCUMENTS

| | | | |
|---|---|---|---|
| CN | 101912450 | 12/2010 | |
| EP | 1688161 A1 * | 8/2006 | ......... A61K 31/4985 |
| EP | 1841442 A1 * | 10/2007 | ............... A61P 3/10 |
| EP | 2 157 176 | 2/2010 | |
| WO | WO 89/012685 | 12/1989 | |
| WO | WO 93/09807 | 5/1993 | |
| WO | WO 95/29148 | 11/1995 | |
| WO | WO 95/30429 | 11/1995 | |
| WO | WO 98/48818 | 11/1998 | |
| WO | WO 01/56532 | 8/2001 | |
| WO | WO 01/59084 | 8/2001 | |
| WO | WO 01/72328 | 10/2001 | |
| WO | WO 02/32461 | 4/2002 | |
| WO | WO 02/100445 | 12/2002 | |
| WO | WO 2004/041296 | 5/2004 | |
| WO | WO 2004/096216 | 11/2004 | |
| WO | WO 2005/007820 | 1/2005 | |
| WO | 2006136963 A2 | 12/2006 | |
| WO | WO 2008/026014 | 3/2008 | |
| WO | WO 2008/055145 | 5/2008 | |
| WO | WO 2008/073603 | 6/2008 | |
| WO | 2009074797 A1 | 6/2009 | |
| WO | WO-2014005183 A1 * | 1/2014 | .............. A61P 37/08 |
| WO | WO 2015/157791 | 10/2015 | |
| WO | WO 2015/157822 | 10/2015 | |

OTHER PUBLICATIONS

Aird , Best Practice & Research Clinical Haematology, 2004, 17/1:161-182 (Year: 2004).*

Xue et al, Pathobiology, 2015, 82:100-106. published online: Jul. 7, 2015 (Year: 2015).*

Sakar et al, Eur J. Histochem.2007, 51:103-109. (Year: 2007).*

Hughes, International Journal of Antimicrobial Agents, 2006, 28:90-94. (Year: 2006).*

Xue et al. "Activated Protein C Enhances Human Keratinocyte Barrier Integrity via Sequential Activation of Epidermal Growth Factor Receptor and Tie2" The Journal of Biological Chemistry vol. 286, No. 8, pp. 6742-6750, Feb. 25, 2011. (Year: 2011).*

Andriessen et al. "Hypertrophic scarring is associated with epidermal abnormalities: an immunohistochemical study" Journal of Pathology, 186:192-200 (1998).

Bae et al. "Thrombin Down-Regulates the TGF-β-Mediated Synthesis of Collagen and Fibronectin by Human Proximal Tubule Epithelial Cells Through the EPCR-Dependent Activation of PAR-1" Journal of Cellular Physiology, 225:233-239 (2010).

English Translation of Office Action corresponding to Chinese Patent Application No. 201480078924.1 (11 pages) (dated Oct. 8, 2019).

Guo et al. "An Activated Protein C Analog Stimulates Neuronal Production by Human Neural Progenitor Cells via a PAR1-PAR3-S1PR1-Akt Pathway" The Journal of Neuroscience, 33(14):6181-6190 (2013).

Herdrich et al. "Fetal Tendon Wound Size Modulates Wound Gene Expression and Subsequent Wound Phenotype" Wound Repairand Regeneration, 18:543-549 (2010).

Jiang et al. "Epidermal growth factor and transforming growth factor alpha specifically induce the activation- and hyperproliferation-associated keratins 6 and 16" Proceedings of the National Academy of Sciences USA, 90:6786-6790 (1993).

Julovi et al. "Protease Activated Receptor-2 Mediates Activated Protein C-Induced Cutaneous Wound Healing via Inhibition of p38" The American Journal of Pathology, 179(5):2233-2242 (2011).

Mosnier et al. "The cytoprotective protein C pathway" Blood, 109:3161-3172 (2007).

Boulaftali et al. "Endothelial Protease Nexin-1 Is a Novel Regulator of A Disintegrin and Metalloproteinase 17 Maturation and Endothelial Protein C Receptor Shedding via Furin Inhibition" Arterioscler Tromb Vac Biol., 33:1647-1654 2013.

Abdou et al. "Immunohistochemical Expression of TGF-β1 in Keloids and Hypertrophic Scars" *American Journal of Dermatopathology* 33(1):84-91 (2011).

Al-Khawajah, Marwan M. "Failure of Interferon-Alpha 2B in the Treatment of Mature Keloids" *International Journal of Dermatology* 35(7):515-517 (1996).

Altschul et al. "Gapped BLAST and PSI-BLAST: a new generation of protein database search programs" *Nucleic Acids Research* 25(17):3389-3402 (1997).

Berth-Jones et al. "Vitamin D analogues and psoriasis" *British Journal of Dermatology* 127:71-78 (1992).

Bettinger et ai. "The Effect of TGF-β on Keioid Fibroblast Proliferation and Collagen Synthesis" Plastic and Reconstructive Surgery 98(5):827-833 (1996).

Bush et al. "Therapies with Emerging Evidence of Efficacy: Avotermin for the Improvement of Scarring" *Dermatology and Research Practice* 2010:1-6 (2010).

Cabrijan et al. "Psoriasis Vulgaris—An Inflammatory Skin Disease and/or Benign Epidermal Hyperplasia" *Acta Dermatovenerologica Croatica* 19(2):117-119 (2011).

Chalmers, Richard L "The evidence for the role of transforming growth factor-beta in the formation of abnormal scarring" *International Wound Journal* 8:218-223 (2011).

Chiricozzi et al. "Integrative Responses to IL-17 and TNF-α in Human Keratinocytes Account for Key Inflammatory Pathogenic Circuits in Psoriasis" *Journal of Investigative Dermatology* 131:677-687 (2011).

Cordeiro et al. "Novel antisense oligonucleotides targeting TGF-β inhibit in vivo scarring and improve surgical outcome" *Gene Therapy* 10:59-71 (2003).

Esmon, Charles T. "Crosstalk between inflammation and thrombosis" *Maturitas* 47:305-314 (2004).

Esmon, Charles T. "Structure and functions of the endothelial cell protein C receptor" *Critical Care Medicine* 32[Suppl.]:S298-S301 (2004).

Feistritzer et al. "Endothelial barrier protection by activated protein C through PAR1-dependent sphingosine 1-phosphate receptor-1 crossactivation" *Blood* 105:3178-3184 (2005).

Ferguson et al. "Scar-free healing: from embryonic mechanisms to adult therapeutic intervention" *Philosophical Transactions of the Royal Society B: Biological Sciences* 359(1445):839-850 (2004).

Finigan et al. "Activated Protein C Mediates Novel Lung Endothelial Barrier Enhancement" *The Journal of Biological Chemistry* 280(17):17286-17293 (2005).

(56) References Cited

OTHER PUBLICATIONS

Freedberg et al. "Keratins and the Keratinocyte Activation Cycle" *The Journal of Investigative Dermatology* 116(5):633-640 (2001).
Fukushiro, Torii "Characteristics of cultured cells of human epidermal keratinocytes from hypertrophic scars and of its apoptosis" *Proceedings from the 13th Conference on Disorders of Keratinisation*(12 pages) (1999).
Guo et al. "Neuroprotective activities of activated protein C mutant with reduced anticoagulant activity" *European Journal of Neuroscience* 29:1119-1130 (2009).
Herrier, Richard N. "Advances in the treatment of moderate-to-severe plaque psoriasis" *American Journal of Health-System Pharmacy* 68:795-806 (2011).
Honardoust et al. "Reduced Decorin, Fibromodulin, and Transforming Growth Factor-β3 in Deep Dermis Leads to Hypertrophic Scarring" *Journal of Burn Care & Research* 33(2):218-227 (2012).
International Search Report and the Written Opinion of the International Searching Authority corresponding to International Patent Application No. PCT/AU2013/000729 (9 pages) (dated Jul. 18, 2013).
Jackson et al. "Activated protein C prevents inflammation yet stimulates angiogenesis to promote cutaneous wound healing" *Wound Repair and Regeneration* 13(3):284-294 (2005).
Kerschen et al. "Endotoxemia and sepsis mortality reduction by non-anticoagulant-activated protein C" *The Journal of Experimental Medicine* 204(10):2439-2448 (2007).
Kur-Piotrowska et al. "Neotenic phenomenon in gene expression in the skin of Foxn1- deficient (nude) mice—a projection for regenerative skin wound healing" *BMC Genomics* 18(56):1-15 (2017).
Kurian et al. "Current Effective Topical Therapies in the Management of Psoriasis" *Skin Therapy Letter* 16(1):4-7 (2011).
Kuroda et al. "Altered Expression of Angiopoietins and Tie2 Endothelium Receptor in Psoriasis" *Journal of Investigative Dermatology* 116:713-720 (2001).
Lay et al. "Acute inflammation is exacerbated in mice genetically predisposed to a severe protein C deficiency" *Blood* 109:1984-1991 (2007).
Le et al. "Transforming Growth Factor Beta 3 Is Required for Excisional Wound Repair in Vivo" *PLoS One* 7(10):1-10 (2012).
Ledon et al. "Intralesional Treatment for Keloids and Hypertrophic Scars: A Review" *Dermatologic Surgery* 39:1745-1757 (2013).
Lee et al. "Expression of Transforming Growth Factor Beta 1, 2, and 3 Proteins in Keloids" *Annals of Plastic Surgery* 43(2):179-184 (1999).
Lin et al. "Exogenous Transforming Growth Factor-Beta Amplifies Its Own Expression and Induces Scar Formation in a Model of Human Fetal Skin Repair" *Annals of Plastic Surgery* 222(2):146-154 (1995).
Machesney et al. "Activated Keratinocytes in the Epidermis of Hypertrophic Scars" *American Journal of Pathology* 152(5):1133-1141 (1998).
Matsumoto et al. "Activated protein C modulates the proinflammatory activity of dendritic cells" *Journal of Asthma and Allergy* 8:29-37 (2015).
McCollum et al. "Randomized Phase II clinical trial of avotermin versus placebo for scar improvement" *The British Journal of Surgery* 98(7):925-934 (2011).
McCoy et al. "In Vitro Inhibition of Cell Growth, Collagen Synthesis, and Prolyl Hydroxylase Activity by Triamcinolone Acetonide" *Proceedings of the Society for Experimental Biology and Medicine* 163(2):216-222 (1980).
McKelvey et al. "Activated protein C: A regulator of human skin epidermal keratinocyte function" *World Journal of Biological Chemistry* 5(2): 169-179 (2014).
Momtazi et al. "A nude mouse model of hypertrophic scar shows morphologic and histologic characteristics of human hypertrophic scar" *Wound Repair and Regeneration* 21(1):77-87 (2013).
Montesu et al. "Adverse reactions during biological drug therapy in psoriasis: clinical series and a review of the literature" *G. Itai. Dermatol. Venereol.* 146(4):273-281 (2011) (Abstract Only).

Mosnier et al. "Activated protein C variants with normal cytoprotective but reduced anticoagulant activity" *Blood* 104(6):1740-1744 (2004).
Mosnier et al. "Protein C anticoagulant activity in relation to anti-inflammatory and anti-apoptotic activities" *Frontiers in Bioscience* 11:2381-2399 (2006).
Nestle et al. "Skin immune sentinels in health and disease" *Nature Reviews Immunology* 9(10):679-691 (2009).
O'Brien et al. "Activated Protein C Decreases Tumor Necrosis Factor-Related Apoptosis-Inducing Ligand by an EPCR—Independent Mechanism Involving Egr-1/Erk-1/2 Activation" *Arteriosclerosis, Thrombosis, and Vascular Biology* 27(12):2634-2641 (2007).
Occleston et al. "Prevention and reduction of scarring in the skin by Transforming Growth Factor beta 3 (TGFβ3): from laboratory discovery to clinical pharmaceutical" *Journal of Biomaterials Science, Polymer Edition* 19(8):1047-1063 (2008).
Office Action corresponding to Russian Patent Application No. 2015103510 (12 pages) (dated Dec. 8, 2017).
Pasparakis, Manolis "Regulation of tissue homeostasis by NF-κB signalling: implications for inflammatory diseases" *Nature Reviews Immunology* 9:778-788 (2009).
Pasparakis, Manolis "Role of NF—κB in epithelial biology" *Immunological Reviews* 246:346-358 (2012).
Pearson, William R. "Searching Protein Sequence Libraries: Comparison of the Sensitivity and Selectivity of the Smith-Waterman and FASTA Algorithms" *Genomics* 11(3):635-650(1991).
Profyris et al. "Cutaneous scarring: Pathophysiology, molecular mechanisms, and scar reduction therapeutics Part I. The molecular basis of scar formation" *Journal of the American Academy of Dermatology* 66(1):1-10 (2012).
Shah et al. "Neutralising antibody to TGF-$\beta_{1,2}$ reduces cutaneous scarring in adult rodents" *Journal of Cell Science* 107:1137-1157 (1994).
Skripin, Y.K. "Skin and Venereal Diseases" M, Triada-X, p. 363 (2000).
Smith et al. "Identification of Common Molecular Subsequences" *Journal of Molecular Biology* 147(1):195-197 (1981).
Thompson et al. "Genetic Risk Factors for Hypertrophic Scar Development" *Journal of Burn Care& Research* 34(5):477-482 (2013).
Tran et al. "Insight into psoriasis management: Commercial perspectives for the U.S. psoriasis market" *Journal of Dermatological Treatment* 22:18-26 (2011).
Uchiba et al. "Activated Protein C Induces Endothelial Cell Proliferation by Mitogen-Activated Protein Kinase Activation In Vitro and Angiogenesis In Vivo" *Circulation Research* 95:34-41 (2004).
Van Zonneveld et al. "Inflammation, vascular injury and repair in rheumatoid arthritis" *Annals of the Rheumatic Diseases* 69(Suppl. 1):i57-i60 (2010).
Vetrano et al. "Unexpected role of anticoagulant protein C in controlling epithelial barrier integrity and intestinal inflammation" *Proceedings of the National Academy of Sciences* 108(49):19830-19835 (2011).
Walker et al. "Activated protein C analog with reduced anticoagulant activity improves functional recovery and reduces bleeding risk following controlled cortical impact" *Brain Research* 1347:125-131 (2010).
Wallis, Robert S. "Biologies and Infections: Lessons from Tumor Necrosis Factor Blocking Agents" *Infectious Disease Clinics of North America* 25:895-810 (2011).
WANG et ai. "An Activated Protein C Analog With Reduced Anticoagulant Activity Extends the Therapeutic Window of Tissue Plasminogen Activator for Ischemic Stroke in Rodents" *Stroke* 43(9):2444-2449 (2012).
White et al. "Activated protein C inhibits lipopolysaccharide-induced nuclear translocation of nuclear factor κB (NF-κB) and tumour necrosis factor α (TNF-α) production in the THP-1 monocytic cell line" *British Journal of Haematology* 110:130-134 (2000).
Williams et al. "Preclinical Safety and Pharmacokinetic Profile of 3K3A-APC, a Novel, Modified Activated Protein C for Ischemic Stroke" *Current Pharmaceutical Design* 18(27):4215-4222 (2012).

(56) References Cited

OTHER PUBLICATIONS

Xia et al. "Complex epithelial-mesenchymal interactions modulate transforming growth factor-β expression in keloid-derived cells" *Wound Repair and Regeneration* 12(5):546-556 (2004).

Xu et al. "Comparison of the mechanisms of intralesional steroid, interferon or verapamil injection in the treatment of proliferative scars" Zhonghua zhengxing waike zazhi 25(1):37-40 (2009) (Abstract Only).

Xue et al. "Activated protein C stimulates proliferation, migration and wound closure, inhibits apoptosis and upregulates MMP-2 activity in cultured human Keratinocytes" *Experimental Cell Research* 299:119-127 (2004).

Xue et al. "Endothelial Protein C Receptor and Protease-Activated Receptor-1 Mediate Induction of a Wound-Healing Phenotype in Human Keratinocytes by Activated Protein 0" *Journal of investigative Dermatology* 125:1279-1285 (2005).

Xue et al. "Differential Regulation of Matrix Metalloproteinase 2 and Matrix Metalloproteinase 9 by Activated Protein C" *Arthritis& Rheumatism* 56(9):2864-2874 (2007).

Xue et al. "Endothelial protein C receptor is Overexpressed in rheumatoid arthritic (RA) synovium and mediates the anti-inflammatory effects of activated protein C in RA monocytes" *Annals of the Rheumatic Diseases*66:1574-1580 (2007).

Xue et al. "Protein C Is an Autocrine Growth Factor for Human Skin Keratinocytes" *The Journal of Biological Chemistry* 282(18):13610-13616 (2007).

Xue et al. "Activated Protein C Enhances Human Keratinocyte Barrier Integrity via Sequential Activation of Epidermal Growth Factor Receptor and Tie2" *The Journal of Biological Chemistry* 286(8):6742-6750 (2011).

Yuksel et al. "Activated Protein C Inhibits Lipopolysaccharide-Induced Tumor Necrosis Factor-a Production by Inhibiting Activation of both Nuclear Factor-κB and Activator Protein-1 in Human Monocytes" *Thrombosis and Haemostasis* 88:267-273 (2002).

Zaba et al. "Identification of TNF-related apoptosis-inducing ligand and other molecules that distinguish inflammatory from resident dendritic cells in patients with psoriasis" *Journal of Allergy and Clinical Immunology* 125(6):1261-1268 (2010).

Zanni, Guido "Psoriasis: issues far more serious than cosmetic" *The Consultant Pharmacist* 27(2):86-88, 90, 93-86 (2012) (Abstract Only).

Kerschen et al., "Endotoxemia and Sepsis Mortality Reduction by Non-Anticoagulant-Activated Protein C", The Journal of Experimental Medicine, vol. 204, No. 10, Oct. 1, 2007, 2439-2448.

Matsumoto, et al., "Activated Protein C Modulates the Proinflammatory Activity of Dendritic Cells", Journal of Asthma and Allergy, 2015:8, 29-37.

* cited by examiner

TREATMENT OF INFLAMMATORY SKIN DISORDERS

FIELD OF THE INVENTION

The invention relates to skin disorders characterised by hyperproliferation of keratinocytes, including but not limited to psoriasis and to treatment of same.

BACKGROUND OF THE INVENTION

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

Psoriasis, the most prominent autoimmune disease, is both chronic and relapsing in nature. It is characterized by impaired barrier function, hyperproliferation of epidermal keratinocytes and pronounced infiltration of inflammatory cells.

Recent data showed that although inflammatory T cells are integral to the disease, the keratinocyte is the key driver of pathogenic inflammation in psoriasis, through integrating responses to interleukin (IL)-1, IL-6, IL-8, IL-17, interferon (INF)-γ, and TNF-α (1,2) and the activation of nuclear factor NF-κB, a signaling molecule that maintains immune homeostasis of epidermal keratinocytes (3,4).

There is no cure for psoriasis. Topical medications, phototherapy, traditional systemic agents, and biologics only offers options for management of its symptoms. A combination of agents is frequently needed for moderate-to-severe cases and positive long-term outcomes require medication adherence (5).

Typically, localized disease (10% body surface area) is managed with topical medications while larger areas require phototherapy or systemic therapy. Disease localized to the palm and soles is often treated systemically, since skin thickness in this area is not amenable to topical therapy.

Topical treatment agents include corticosteroids such as clobetasol, and a vitamin D analogue such as calcitriol or calcipotriene (6,7). The corticosteroid works by decreasing inflammation, suppressing mitotic activity, and causing vasoconstriction in the targeted area. The mechanism of vitamin D analogues action is not fully understood, but it appears to regulate keratinocyte proliferation and differentiation (6). Thus components of both treatments include inhibition of cell proliferation, although this is non specific.

Topical corticosteroids can cause skin atrophy, irritation, and dryness in the affected area. Vitamin D analogues are generally safe but can cause irritation while there is a risk of hypercalcemia if used in very large doses (8).

With extensive psoriatic disease, phototherapy or systemic treatments are used. The first-line treatment for extensive psoriasis is through ultraviolet light, such as UVB and UVA. However, this treatment is associated with a greater risk of burns and skin cancer, particularly in patients with lighter skin color. Low-dose methotrexate can also be used if UV light therapy proves ineffective. Methotrexate is reasonably effective at controlling psoriasis, but is severely limited by serious toxic effects.

With the increasing knowledge of the immune nature of the disease, biological agents that target T lymphocytes, TNF-α, IL-12, and IL-23 have been successfully utilized in moderate-to-severe psoriasis (8). Three commonly used TNF inhibitors include Enbrel (etanercept), Humira (adalimumab), and Remicade (infliximab). Ustekinumab, a new agent that targets IL-12 and IL-23 was approved for marketing in 2009, offering similar efficacy and safety profiles to anti-TNF agents (9).

Biological agents offer considerable advantages over previously available systemic therapies, however, clinical trials of these drug demonstrated that the activity of such compounds is accompanied in the long term by a number of disadvantages (10-11). Firstly, in patients with latent *Mycobacterium tuberculosis* (TB) infection, active TB may develop soon after the initiation of treatment with infliximab. In addition, patients on TNF inhibitors are at increased risk of opportunistic fungal infections, such as pulmonary and disseminated histoplasmosis, coccidioidomycosis, and blastomycosis. Secondly, a dose-dependent increased risk of malignancies including lymphoma and skin cancer applies to some treatments. Thirdly, a proportion of patients do not respond to the agents, or fail to maintain initial response. The availability of the biological agent is also limited by its high economical cost.

Activated protein C (APC) induces the gene expression of the anti apoptotic human genes bcl-2 and MIHB. Based on this anti-apoptotic function, APC has been mentioned for minimisation of apoptosis in a wide range of conditions where apoptosis is of concern, including a large range of organ specific and non specific inflammatory diseases, autoimmune diseases, neoplasia and infectious disease. Notably the use of APC is not suggested to treat all symptoms of disease in these condition, merely to minimise apoptosis (see WO2001/072328).

Further, many in the field are of the view that the anti-apoptotic effects, such as suggested in WO2001/072328, should make APC unsuitable for treatment of disorders where there is dysfunctional regulation of cell proliferation, especially disorders involving keratinocyte hyperproliferation. In particular, it is known that, apart from the attenuation of calcium-induced cell death via prevention of cell apoptosis by APC, APC also has a potent stimulatory effect on keratinocyte proliferation, and APC promotes keratinocyte survival, growth and migration in an autocrine manner via EPCR, epidermal growth factor receptor and activation of ERK1/2 (17, 20).

There is a need for new approaches and therapies for treatment of, or for minimising progression or symptoms of, disease or disorders characterised by keratinocyte hyperproliferation, such as psoriasis.

SUMMARY OF THE INVENTION

The invention seeks to address one or more of the above problems or limitations, and in certain embodiments provides a method of treating an individual for a skin disorder characterised by the presence of hyperproliferative keratinocytes including:
 providing an individual having a region of skin characterised by the presence of hyperproliferative keratinocytes;
 contacting the region of skin with a therapeutically effective amount of activated protein C (APC);
 thereby treating the individual for the skin disorder.

In other embodiments there is provided a method of treating an individual for psoriasis including:
 providing an individual having a psoriatic plaque;
 applying a composition including a therapeutically effective amount of activated protein C (APC) to the plaque;
 thereby treating the individual for psoriasis.

In other embodiments there is provided a method of treating an individual for acne including:
providing an individual having acne;
applying a composition including a therapeutically effective amount of activated protein C (APC) to the acne;
thereby treating the individual for acne.

In other embodiments there is provided a method of treating an individual for atopic dermatitis including:
providing an individual having atopic dermatitis;
applying a composition including a therapeutically effective amount of activated protein C (APC) to the atopic dermatitis or region of skin containing same;
thereby treating the individual for atopic dermatitis.

In other embodiments there is provided a method of treating an individual for Pyoderma gangrenosam including:
providing an individual having Pyoderma gangrenosam;
applying a composition including a therapeutically effective amount of activated protein C (APC) to the Pyoderma gangrenosam or region of skin containing same;
thereby treating the individual for Pyoderma gangrenosam.

In another embodiment there is provided a method of inducing wound healing or tissue regeneration in a region of skin having a disorder characterised by keratinocyte hyperproliferation including:
providing an individual having a region of skin having a disorder characterised by the presence of hyperproliferative keratinocytes;
contacting the region of skin with a therapeutically effective amount of activated protein C (APC);
thereby inducing wound healing or tissue regeneration in the skin region.

In further embodiments there is provided a composition including a therapeutically effective amount of APC for use in minimising a skin disorder characterised by the presence of hyperproliferative keratinocytes, or for treatment of psoriasis, acne or atopic dermatitis, in an individual.

In still further embodiments there is provided a use of APC in the manufacture of a medicament for minimising a skin disorder characterised by the presence of hyperproliferative keratinocytes, or for treatment of psoriasis, acne or atopic dermatitis in an individual.

In still further embodiments there is provided a use of APC for minimising a skin disorder characterised by the presence of hyperproliferative keratinocytes, or for treatment of psoriasis, acne or atopic dermatitis in an individual.

In still further embodiments there is provided a kit including a composition including a therapeutically effective amount of APC and written instructions for use of the APC in a method of treatment of a disorder characterised by the presence of hyperproliferative keratinocytes, or for treatment of psoriasis, acne or atopic dermatitis in an individual, the method being as described herein.

DETAILED DESCRIPTION OF THE EMBODIMENTS

Figure 1:
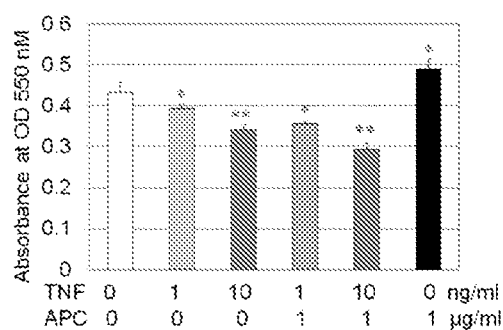
FIG. 1. (A) Human neonatal foreskin keratinocytes were pre-treated with APC for 4 hr, then TNF-α and cells were incubated for 72 hours and proliferation detected by MTT assay. *$P<0.05$, **$P<0.01$ compared to relevant control. (B) Effect of APC on growth of normal mouse dermal fibroblasts (MDF), normal human dermal fibroblasts (HDF) and human rheumatoid synovial fibroblasts (RSF, in red), measured using a crystal violet assay (mean±SD. N=4 separate experiments. *, ‡, #$p<0.01$ compared to relevant control, ANOVA. (C) RSF were treated with APC for 24 hr. p21 and p27 measured by western blotting.
Figure 1:
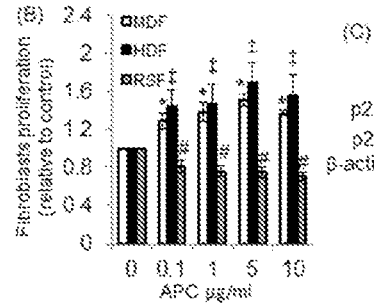
Figure 1:
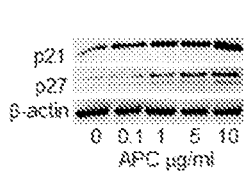
Figure 2:
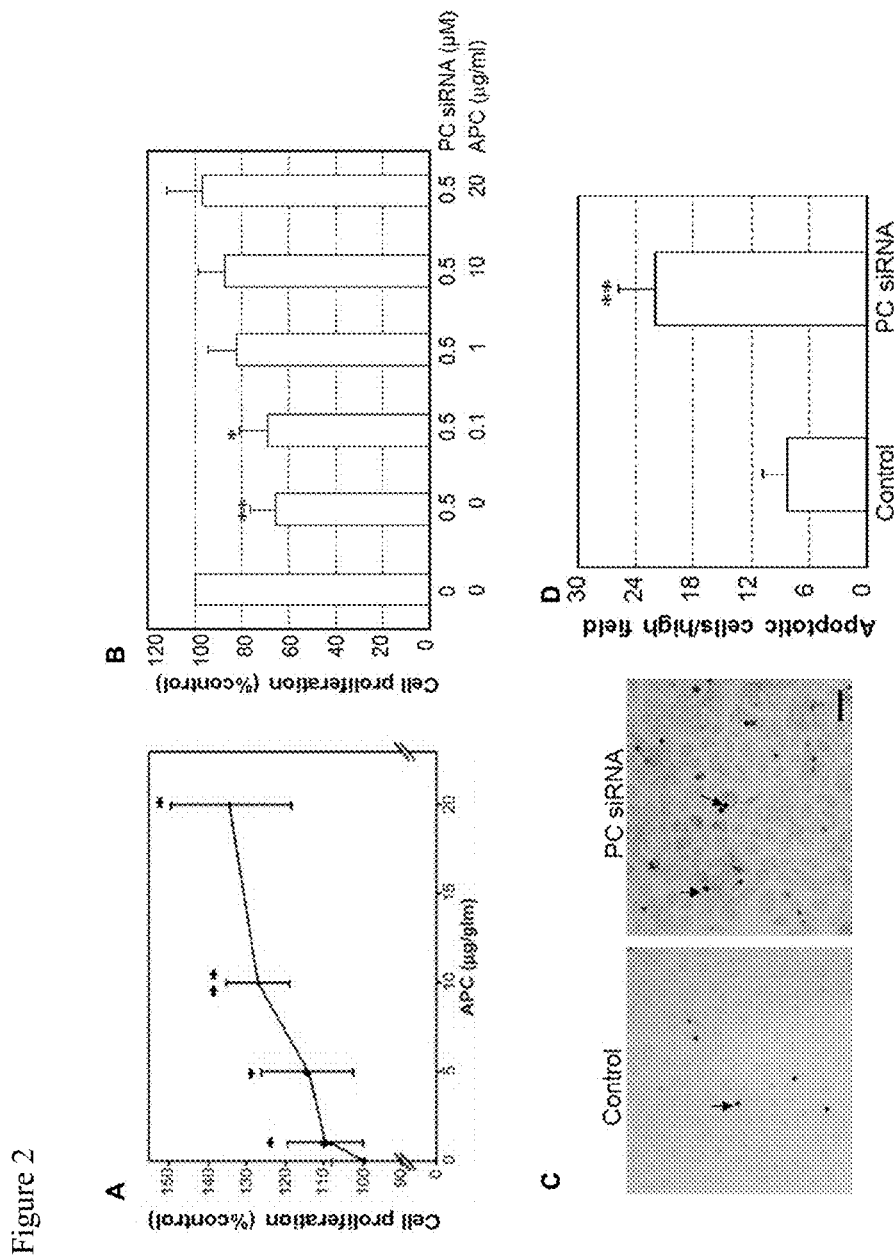
FIG. 2: Exogenous or endogenous APC stimulates proliferation and prevents apoptosis of cultured keratinocyte. A) Proliferation was measured using an MTT assay and data expressed as % cell proliferation compared to control. B) Proliferation of keratinocytes in response to PC siRNA and APC treatment after 72 h as detected by MIT assay. Cell proliferation is expressed as a percentage of control. C&D) Keratinocytes were treated with PC siRNA (0.5 μm). After 48 h, cells were used for a TUNEL (terminal dUTP nick-end labeling) assay to detect apoptotic cells (black arrows indicate apoptotic cells) (C) and quantitated by counting apoptotic cells under high power microscopy (×20) (D). Data were expressed as the average number of apoptotic cells per field of 15 fields (mean±S.E., n=3). Graphs represent one of three independent experiments. Images represent one of three independent experiments. * $p<0.05$, ** $p<0.01$. Scale bar: 40 μm.
Figure 3:
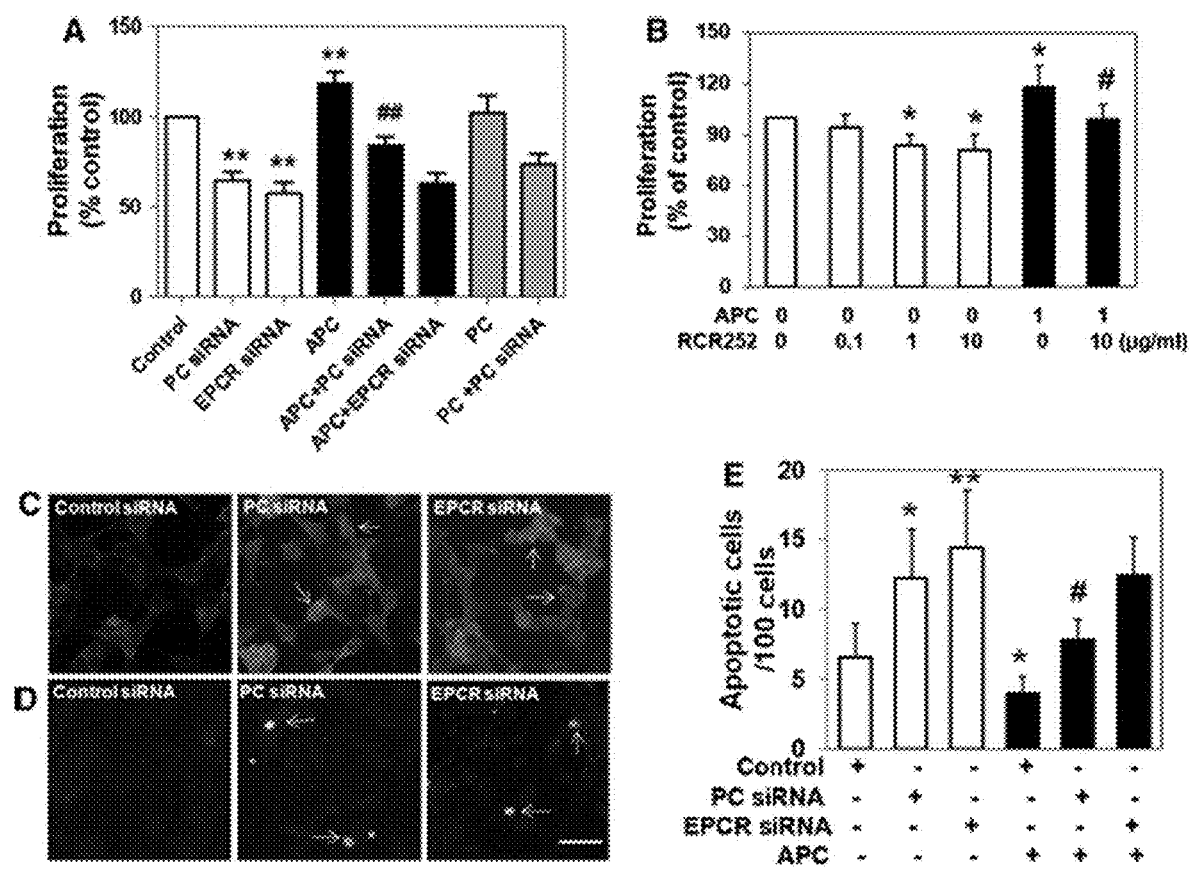
FIG. 3: PC or EPCR siRNA treatment inhibits growth and promotes apoptosis of HUVEC.A) Proliferation rate of HUVEC in response to control, PC siRNA or EPCR siRNA (500 nM) treatment in the presence or absence of exogenous APC or PC, as detected by MTT assay. Cell proliferation is expressed as a percentage of control (mean±SD) over 72 h. **$P<0.01$ compared to control (1st bar), ##$P<0.01$ compared to PCsiRNA (2nd Bar). B) Proliferation of HUVEC in response to a blocking antibody to EPCR (RCR252) in the presence or absence of recombinant APC. Cell proliferation is expressed as a percentage of control (mean±SD) over 72 h. *$P<0.05$ compared to control (1st bar), #$P<0.05$ compared to APC alone (5th bar). C-E) HUVEC were treated with control, PC siRNA or EPCR siRNA (both at 500 nM). After 36 h, transfected cells treated with recombinant APC (1 μg/ml) for 12 h, and cells were harvested at 48 h. Active caspase-3 was detected by immunofluorescent staining (white arrows indicate active caspase-3 positive cells) (C) and apoptotic cells were detected by in situ cell death detection kit (white arrows indicate apoptotic cells) (D). Images represent one of three independent experiments. Scale bar 40 μm. E) Apoptotic cells (from D) were quantitated by counting cells co-stained with DAPI under the microscopy. Data are expressed as the average number of apoptotic cells under a high magnification (40×) (mean±SEM n=3). *$P<0.05$, **$P<0.01$ compared to control (1st bar), $P<0.05$ compared to PCsiRNA treatment (2nd bar)

As previously mentioned, at the time of the invention, keratinocytes were understood to be critically involved in the pathology of a range of skin inflammatory disorders including psoriasis. Many of the long standing anti-inflammatory therapies were understood to beneficially minimise the replication of inflammatory cells, and given that inhibition of growth and/or replication of inflammatory cells is preferred, those compounds which had been predicted to be anti-apoptotic were not considered for clinical use in the treatment of these disease. These are some of the reasons why, in spite of an anti-inflammatory function, prior to this invention, APC had never been suggested to minimise or resolve the skin disorders characterised by hyperproliferative, hyperplastic or otherwise disregulated proliferation of keratinocytes. Indeed, prior to the invention, the published data on APC's stimulatory effect on keratinocyte proliferation was seen to imply that APC therapy would be detrimental for inflammatory skin diseases such as psoriasis, acne and other skin disorders characterised by keratinocyte hyperproliferation.

As described herein, the inventor has surprisingly found that APC inhibits apoptosis in slow growing or normal human keratinocytes or cells but has no effect on inhibiting the proliferation of abnormal or fast growing keratinocytes or cells, the latter being the mediators of a wide range of inflammatory skin disorders.

From this, the inventor has recognised that in skin disorders associated with keratinocyte hyperproliferation, two populations' of keratinocytes with respect to response to anti-apoptotic APC-mediated signals are in existence. Specifically, those that respond to APC (i.e. that do not undergo apoptosis in response to basal levels of APC) are slow growing, normal, non inflammatory cells. Further, those that respond to APC (i.e. that do undergo apoptosis in response to basal levels of APC) are faster growing, abnormal inflammatory cells.

Importantly, the inventor has discovered that whilst APC can stimulate proliferation of slower growing normal cells, it has a unique selective ability to inhibit proliferation of fast growing cells. Data is shown herein in which APC enhances proliferation and inhibits apoptosis of slow-growing or normal human cells under basal conditions, including endothelium and keratinocytes. However, according to the invention, APC differentially regulates cell proliferation depending on the inflammatory state of the cells—specifically APC inhibits growth of TNF-α-stimulated keratinocytes and fast growing synovial fibroblasts from rheumatoid arthritic synovium.

From the work described herein, the inventor has conceived that, contrary to the understanding of the literature prior to the invention, the anti-inflammatory benefits of APC might be realised in patients requiring treatment of skin disorders characterised by keratinocyte hyperproliferation, because while the anti-inflammatory effect would apply to the inflammatory cells, the anti-apoptotic effect should apply selectively or specifically to the keratinocytes that are non inflammatory, and not to inflammatory keratinocytes.

Further, the outcome of such treatment should be the continued normal proliferation of non inflammatory keratinocytes (arising from the anti-apoptotic function of APC) and through administration of APC, the provision of conditions including anti inflammation, together with possibility of allowing inflammatory, hyperproliferative keratinocytes to become apoptotic.

A. Definitions

As used herein, except where the context requires otherwise, the term "comprise" and variations of the term, such as "comprising", "comprises" and "comprised", are not intended to exclude further additives, components, integers or steps.

"Keratinocyte" generally refers to an epidermal cell that synthesizes keratin and other proteins and sterols. These cells constitute 95% of the epidermis, being formed from undifferentiated, or basal cells at the dermal-epidermal junction. Its characteristic intermediate filament protein is cytokeratin. In its various successive stages, keratin forms the prickle cell layer and the granular cell layer, in which the cells become flattened and slowly die to form the final layer, the stratum corneum, which gradually exfoliates.

"Hyperproliferation" generally refers to an abnormally high rate of proliferation of cells by rapid division. Hyperproliferation in some contexts may arise from a cell largely existing in $G_1$, S or $G_2$ phases of the cell cycle. Hyperproliferation may also be referred to as hyperplasia, and hyperproliferative cells may be referred to as hyperplastic cells or tissue.

"Hyperproliferative keratinocytes" are generally keratinocytes that tend to exist in a stage of interphase of the cell cycle, such as $G_1$, S or $G_2$. These cells are unlike normal keratinocytes in that normal keratinocytes generally exist in $G_0$ (Gap zero), which is either a stage separate from interphase or an extended $G_1$ phase, which follows the restriction point, a cell cycle checkpoint found at the end of $G_1$. Hyperproliferative keratinocytes are also generally characterised by having a expression of inflammatory genes and in particular, genes involved in the NF-κB signaling pathway.

"Normal keratinocytes" are generally keratinocytes that tend to exist in $G_0$, or in an extended $G_1$ phase. Generally these keratinocytes are typically of those that have not been stimulated with TNF-α, and they do not generally have expression of genes of the NF-κB signaling pathway.

"Activated protein C" or "APC" generally refers to a serine protease that functions as an anticoagulant by binding to protein S and proteolytically inactivating factors Va and VIIIa and by stimulating fibrinolysis through neutralization of a plasminogen activator inhibitor. Walker et al., FASEB J. 6, 2561-2567 (1992); Esmon, Arterioscler. Thromb. 12, 135-145 (1992); van Hinsbergh et al., Blood 65, 444-451 (1985). Precursor protein C is produced primarily in the liver. Activation is achieved by the removal of a dodecapeptide at the N-terminus of the heavy chain of protein C. The protein C pathway is initiated when thrombin binds to the endothelial cell surface protein, thrombomodulin, and protein C binds to the endothelial cell protein C receptor. By inactivating factors Va and VIIIa, APC limits the amount of thrombin formed. Esmon, Arterioscler. Thromb. 12, 135-145 (1992).

"Treating" and "treatment" generally refers to the management and care of a patient for the purpose of combating a disease, condition, or disorder whether to eliminate the disease, condition, or disorder, or prophylactically to prevent the onset of the symptoms or complications of the disease, pathological condition, or disorder.

A "skin disorder characterised by the presence of hyperproliferative keratinocytes" generally refers to a disease, condition, syndrome or the like in which there is a predominance of hyperproliferative keratinocytes, and in particular an abundance of hyperproliferative keratinocytes as compared with normal tissue. The disorder may be an inflammatory disorder, and typically involving one or more of the stratum basale (stratum germinativum), stratum spinosum, stratum granulosum, stratum lucidum and stratum corneum. Examples of skin disorders include pustular (suppurative) and non pustular (non suppurative) psoriasis, including the forms described herein, and acne including acne vulgaris or cystic acne.

A "therapeutically effective amount" generally refers to an amount of pharmaceutical compound that provides for the desired clinical outcome. In certain embodiments, a therapeutically effective amount of APC generally provides an anti-apoptotic effect on normal keratinocytes and may or may not provide an apoptotic effect on hyperproliferative keratinocytes. In one embodiment, a therapeutically effective amount of APC may stop proliferation of hyperproliferative keratinocytes and/or provide an anti-inflammatory effect. The relevant amounts can be established or determined according to the methods of the invention disclosed herein.

A "apoptosis inducing amount" generally refers to an amount of APC that provides for induction of apoptosis of a hyperproliferative keratinocyte.

A "growth stimulatory amount" generally refers to an amount of APC that provides for induction of proliferation of non hyperproliferative keratinocytes, and in particular, slow growing, normal, non inflammatory keratinocytes.

An "anti-inflammatory amount" generally refers to an amount of APC that provides for minimisation of inflammation of a skin disorder characterised by hyperproliferative keratinocytes.

B. Methods of Treatment

With the understanding that APC does not prevent inflammatory hyperproliferative keratinocytes from undergoing apoptosis, the inventor has recognised that APC can be used to provide anti-inflammatory effects to disorders such as psoriasis and acne without aggravating or worsening these conditions as would otherwise occur if inflammatory keratinocytes were prevented from apoptosis or otherwise induced to proliferate or grow, as previously thought prior to this invention. Therefore, in certain embodiments there is provided a method of treating an individual for a skin disorder characterised by the presence of hyperproliferative keratinocytes. The method includes:
  providing an individual having a region of skin characterised by the presence of hyperproliferative keratinocytes;
  contacting the region of skin with a therapeutically effective amount of activated protein C (APC);
  thereby treating the individual for the skin disorder.

According to the method, the APC is delivered directly to the site or region of the skin characterised by the presence of hyperproliferative keratinocytes by contacting the APC or formulation containing same with the relevant region. The site or region may be an open wound or ruptured skin surface as occurs in acne or pustular psoriasis, or it may not be substantially ruptured, i.e. it may be more like a plaque or other raised, hardened or fibrotic tissue. Where the site or region is open in the sense of being ruptured or like, the APC may be applied to the surface surrounding the rupture and/or to the exposed tissue that normally underlies the skin surface (for example, stratum basale (stratum germinativum), stratum spinosum, stratum granulosum, stratum lucidum).

In this context, an important finding of the inventor has been that APC can be delivered at the required site where the skin is substantially unbroken, for example at a region surrounding a rupture pustule, or at an otherwise substantially unruptured skin surface. This enables local delivery by direct contact of the APC or relevant formulation with the site, something that is quite distinct from previous clinical systemic applications of APC in treatment of a disseminated disease or condition such as sepsis. The local administration of APC according to the invention is advantageous and applicable to diseases which are local rather than disseminated or systemic as it limits the risk associated with APC delivery to the local region, and substantially minimises the risks associated with the systemic delivery of APC, for example by continuous infusion.

The local delivery of APC to the site of concern is a significant departure from the administration of APC known in the art for treatment of other diseases and conditions. According to the methods known in the art at the time of this invention, APC is preferably administered parenterally, most preferably intravenously, at a dose of from about 1 µg/day to about 500 mg/day or from about 1 IU/kg/day to about 6000 IU/kg/day for a human patient. See, e.g., U.S. Pat. Nos. 5,151,268 and 5,571,786. For severe sepsis, Xigris™ is administered by continuous infusion at a rate of from about 12 µg/kg/hr to about 30 µg/kg/hr to give a steady state plasma concentration of about 45 ng/ml APC after about two hours of infusion. The current invention generally is not based on a continuous infusion by systemic administration. Rather, it is based a local administration of APC by contacting the region of skin with a therapeutically effective amount of APC as described herein.

The region of skin which is contacted with the therapeutically effective amount of APC may be inflamed, or inflammation may be in recession. In one embodiment, the skin disorder is characterised by one or more, or all of the following processes: apoptosis, inflammation, impaired barrier function.

In one embodiment, the region of skin is inflamed. One particularly important example is a region of skin associated with chronic inflammation. This skin may have the appearance of a psoriatic plaque, and manifest in association with pustules, although the plaque may be substantially non pustular.

The skin disorder may be selected from the group consisting of psoriasis, dermatitis herpetiformis, pemphigus vulgaris, vitiligo, and acne vulgaris or cystic acne.

The skin disorder may be non pustular psoriasis, for example, psoriasis vulgaris or erythrodermic psoriasis.

The skin disorder may be pustular psoriasis, for example, generalized pustular psoriasis, pustolosis palmaris et plantaris, annula postular psoriasis, acrodermatitis continua or impetigo herptiformis.

Typically, where the condition is psoriasis, the region of skin contacted with APC is a psoriatic plaque. Thus, in another embodiment there is provided a method of treating an individual for psoriasis. The method includes:
  providing an individual having a psoriatic plaque;
  applying a composition including a therapeutically effective amount of activated protein C (APC) to the plaque;
  thereby treating the individual for psoriasis.

Where the condition is acne vulgaris, the region of skin contacted with APC may include rupture and unruptured skin. Thus, in another embodiment there is provided a method of treating an individual for acne. The method includes:
  providing an individual having acne;
  applying a composition including a therapeutically effective amount of activated protein C (APC) to the acne;
  thereby treating the individual for acne.

Where the condition is atopic dermatitis, the region of skin contacted with APC may include rupture and unruptured skin. Thus, in another embodiment there is provided a method of treating an individual for atopic dermatitis. The method includes:
  providing an individual having atopic dermatitis;
  applying a composition including a therapeutically effective amount of activated protein C (APC) to the atopic dermatitis;
  thereby treating the individual for atopic dermatitis.

The atopic dermatitis may be a form of eczema selected from the group consisting of endogenous eczema, flexural eczema, infantile eczema, and it may also be known as "prurigo Besnier," "neurodermitis," or "prurigo diathésique".

Notwithstanding the foregoing, it is understood by those skilled in the art that the dosage amount of the APC, protein C, agent that increases the synthesis of protein C, and/or protein C activator will vary with the particular compound or combination of compounds employed, the disease or condition to be treated, the severity of the disease or condition, the type(s) of local administration, the rate of excretion of the compound, the duration of the treatment, the identify of any other drugs being administered to the animal, the age, size and species of the animal, and like factors known in the medical arts. In general, a suitable daily dose of a compound or combination of compounds will be that amount which is the lowest dose effective to produce a therapeutic effect. The dosage amount, dosage form and mode of administration will be determined by an attending physician within the scope of sound medical judgment. Effective dosage amounts, dosage forms, and modes of administration for the various compounds and combination(s) of compounds can be determined empirically and making such determinations is within the skill of the art.

In certain embodiments, it is important that the APC is provided so as to enable contact of APC with skin keratinocytes, as, while not wanting to be bound by hypothesis, it is believed that it is by this contact that the APC provides selective anti-apoptotic activity (i.e. selective to non inflammatory non hyperproliferative cells) of the invention, and anti-inflammatory activity. Generally cells which have been contacted with APC can be recognised by having the following characteristics, higher levels of activated matrix metalloproteinase (MMP)-2 and endothelial protein C receptor (EPCR) and lower activity of activated MAP kinase ERK, and so contact of cells with APC, and therefore, therapeutic efficacy of treatment can be established by assessing for these cell phenotypes.

In certain embodiments, a therapeutically effective amount of APC generally provides an anti-apoptotic effect on normal keratinocytes and an apoptotic effect on hyperproliferative keratinocytes. This outcome can be assessed as follows: measuring cell survival/proliferation (MTT) assay and cell apoptosis (TUNEL assay), thereby establishing whether a therapeutically effective amount of APC has been provided. An exemplary method is shown further herein.

In one embodiment, a therapeutically effective amount of APC may stop proliferation of hyperproliferative keratinocytes and/or provide an anti-inflammatory effect. This outcome can be assessed as follows:
  measuring cell viability/proliferation (MTT assay);
  enzyme linked immunosorbert assay (ELISA) for inflammatory cytokines—IL-1, IL-6, IL-10, IL-17, IL-21/23 or TNF-α or
  ELISA for EPCR (R&D Systems, Inc., MN);
  FACS analysis with propidium iodide (PI) or PI plus annexin for apoptosis;
  Western blot to detect inflammatory signalling molecules such as NF-κB;
thereby establishing whether a therapeutically effective amount of APC has been provided.

In another embodiment, the above outcomes are obtained by establishing a local tissue concentration of APC in the region of skin from 1 ug to 100 mg of APC per g of skin tissues. This can be determined by taking skin punch biopsies under local anaesthetics from the same chronic plaque. The amount of APC may then be determined by methods known in the art. In one example, biopsy tissues are minced and lysed on ice. After centrifugation, the clear supernatants are used to measure the PC concentration by ELISA and APC activity by the chromogenic substrate Spectrozyme PCa assay (American Diagnostica). Enzyme activity is determined by measuring the increase in absorbance of the free chromophore generated per unit time at λ450 nm.

In certain embodiments, the therapeutically effective amount of APC is from 0.1 µg to 5000 µg of APC per $cm^2$ of the region of skin to which the APC is applied, or from 1 µg to 2000 µg of APC per $cm^2$ of the region of skin to which the APC is applied, or from 10 µg to 1000 µg of APC per $cm^2$ of the region of skin to which the APC is applied, or from 10 µg to 200 µg, or from 10 µg to 400 µg, or from 10 µg to 800 µg of APC per $cm^2$ of the region of skin to which the APC is applied The APC may be administered once per week up to twice daily, depending on the nature of the condition. It is generally provided for no more than 20 weeks of consecutive days, or from no more than 6 weeks of consecutive days.

B.1 Methods of Treatment—Topical

Topical treatment methods, for example, using a paste, gel, cream, oil, lotion, foam, ointment or like substance are particularly useful where the relevant skin region is one that contains a ruptured skin surface, as this permits penetration of the APC to the relevant strata of the skin tissue where the inflammatory keratinocytes reside. However, these treatments may also be applied where the skin surface is substantially unruptured for example to a psoriatic plaque.

In one embodiment, the therapeutically effective amount of APC may be from 0.1 to 2000 µg, preferably from 20 to 200 µg of APC per $cm^2$ of the region of skin. A higher amount is generally preferred where the skin is more severely affected, and generally preferred with severe chronic plaque-type psoriasis [Psoriasis Area and Severity index (PAST) of greater than or equal to 12, body surface area (BSA) of greater than or equal to 10] where lesions are present with ulcer, in which APC may promote healing of ulcer. Lower amounts may be preferred where the skin is not severely affected, for example where lesions are present without ulcer.

The concentration of APC in the formulation may be between about 10 ug/ml and 1 mg/ml and the volume of composition applied to the skin region is about 100 ul to 10 ml.

Generally where the relevant condition is psoriasis, the composition is provided to the skin generally with a sterile surface, such as a finger or spatula in a layer of no more than about 10 mm thickness, preferably about 3 mm thickness. It may then be rubbed or massaged into the skin region and surrounding area. The application is generally from once per day to once per week, and generally no longer than 20 weeks, or no longer than 12 weeks.

A similar application procedure and dosage regime may apply to treatment of acne or atopic dermatitis.

In one embodiment, the APC containing composition may be applied to a solid substrate i.e. a bandage, dressing or the like, and the substrate then fixed to the relevant skin region.

B.2 Methods of Treatment—Intradermal Injection

In certain embodiments, the above outcomes are obtained by establishing a local concentration of APC at least 2 times higher than basal line. This amount of APC can be measured by measuring APC activity of skin biopsy using ELISA and chromogenic substrate Spectrozyme PCa assay as mentioned above. Intradermal or subcutaneous injection is generally preferred as an administration route when the stratum corneum is intact and of such nature that there is limited penetration of APC across the topic skin layer. Generally a fine gauge needle on a (~28-34 G) needle on a 1 ml syringe may be used. Multiple injections may be given to cover the surface area of the skin, with ~1 injection per $cm^2$. The amount per injection will vary from 10 µl to 1 ml, with typical amount being 50 µl. Generally the administration is given from once per day to once per week, and generally no longer than 20 weeks. Intradermal or sub cutaneous injection can be used concurrently with topic application of APC. The preferred indication is psoriasis or atopic dermatitis, although other conditions characterised by keratinocyte hyperproliferation may be subject to this treatment.

An exemplary embodiment of subcutaneous/intradermal administration may be useful in severe chronic plaque-type psoriasis [Psoriasis Area and Severity Index (PASI)≥12, body surface area (BSA)≥10] where lesions are present with or without ulcer. APC is administrated subcutaneously at a dose of 200-2000 µg depending on the size of the plaque or lesion, twice a week for 12 weeks followed by a 4-week follow-up period. The injection is performed by 30 gauge needle with total volume of from 500 µl to 5 mls, preferably 1 ml. APC is injected multiple times (intradermally or subcutaneously) at equally-spaced sites surrounding lesion—if lesion was <10 cm$^2$, there are 4 sites and the number of sites and dose increases proportionately with increase in lesion size. APC is dissolved in water to make an isotonic buffered salt solution. If necessary, this treatment can be combined with topical treatment. APC in liquid can be applied on the lesions, daily, continuing for same period of subcutaneous treatment. In both studies (with or without topical treatment) the PAST, static Physician's Global Assessment (sPGA), Dermatology Life Quality Index (DLQI), adverse events, and routine haematological and laboratory values (e.g. cytokine, histological examination, PC/APC activity) can be analysed. Expected outcomes: At week 12, >30% improvement in PAST in all patients and >60% improvement in PASI in 50% of patients is expected.

In one embodiment, an above describe method includes the step of contacting the region of skin with an anti-inflammatory amount of APC.

In one embodiment, an above describe method includes the step of contacting the region of skin with a growth stimulatory amount of APC.

In one embodiment, an above describe method includes the step of contacting the region of skin with an apoptosis inducing amount of APC.

C. APC and Formulations Thereof

APC for use in a method described above may take the form of a composition, or otherwise be obtained by a process, as described below.

APC may be prepared by in vitro activation of protein C purified from plasma or prepared by recombinant DNA techniques by methods well known in the art. See, e.g., U.S. Pat. Nos. 4,981,952, 5,151,268, 5,831,025, 6,156,734, 6,268,344, and 6,395,270.

Alternatively, APC may be prepared directly by recombinant DNA techniques. See, e.g., U.S. Pat. Nos. 4,981,952, 5,151,268, 6, 156,734, 6,268,344 and 6,395,270. Recombinant activated protein C may be produced by activating recombinant human protein C zymogen in vitro or by direct secretion from cells of the activated form of protein C. Protein C may be produced in transgenic animals, transgenic plants, or a variety of eukaryotic cells, including, for example, secretion from human kidney 293 cells as a zymogen then purified and activated by techniques known to the skilled artisan.

APC may be from any species of animal, but human APC is preferred.

Fragments and derivatives of APC may be used in the practice of the invention, provided that they exhibit the activities described herein. See, e.g., U.S. Pat. Nos. 5,151, 268, 5,453,373 and 5,516,650 and PCT applications WO 89/12685, WO 01/56532, WO 01/59084, and WO 01/72328.

APC may be a derivative of human APC having proteolytic, amidolytic, esterolytic, and biological (anticoagulant, anti-inflammatory, or pro-fibrinolytic) activities characteristic of human APC. Examples of protein C derivatives are described by Gerlitz, et al., U.S. Pat. No. 5,453,373, and Foster, et al., U.S. Pat. No. 5,516,650, the entire teachings of which are hereby incorporated by reference.

Suitable pharmaceutical compositions of APC comprise the APC and a pharmaceutically-acceptable carrier. See, e.g., U.S. Pat. Nos. 6,395,270 and 6,159,468 and PCT applications WO 98/48818, WO 01/56532 and WO 01/72328. An APC-containing composition may generally be one that is a stable lyophilized product of high purity comprising a bulking agent (such as sucrose, mannitol, trehalose, and raffinose), a salt (such as sodium chloride and potassium chloride), a buffer (such as sodium citrate, Tris-acetate, and sodium phosphate), and APC. For example, a stable lyophilized composition may comprise a weight ratio of about 1 part APC, between about 7-8 parts salt, and between about 5-7 parts bulking agent. An example of such a stable lyophilized composition is: 5.0 mg APC, 30 mg sucrose, 38 mg NaCl, and 7.56 mg citrate, pH 6.0, per vial.

C.1 Topically Administered Formulation

In one particularly preferred embodiment, the APC is provided in the form of a composition or formulation that is adapted for topical administration to a relevant skin lesion, plaque or other skin surface the subject of the relevant disorder according to a method described under Section B above. Examples of such formulations include those that can be applied directly to the relevant surface enabling local administration of the APC to the relevant site. These formulations include gels, oils, sprays, roll on formulations, ointments, lotions, foams and the like. In one embodiment, the APC is provided in the form of a methyl-cellulose gel and may contained stabilisers such as carbohydrates and salts.

Skin ointment may be a combination of organic, health, beauty or medicinal ingredients, usually in a petroleum oil base. This gives skin ointment a thicker, less water-soluble formula that stays on the surface of the body longer so that the ingredients can work more effectively to treat a wide variety of problems. There are many natural and organic skin ointments which can be ordered from companies (such as Therapex).

Clobetasol propionate (CP) foam (0.05%) may also be used. This is an emulsion aerosol foam that has been used for the treatment of inflammatory and pruritic manifestations of corticosteroid-responsive dermatoses in the United States and for inflammatory and pruritic manifestations of moderate to severe atopic dermatitis in Canada (Olux-E (clobetasol propionate) foam, 0.05% Stiefel Laboratories Inc, Research Triangle Park, N.C. (2011).

Where the formulation is a gel, it may contain APC in an amount of 10-5000 µg/g gel.

C.2 Injectable Formulation

A particularly preferred formulation of APC is the product sold by Eli Lilly and Co., Indianapolis, Ind., under the trademark Xigris™. Xigris™ is supplied as a sterile, lyophilized powder for intravenous infusion. The 5 mg vials of Xigris™ contain 5.3 mg/vial of human recombinant APC, 31.8 mg/vial sucrose, 40.3 mg/vial NaCl, and 10.9 mg/vial sodium citrate, and the 20 mg vials of Xigris™ contain 20.8 mg/vial of human recombinant APC, 124.9 mg/vial sucrose, 158.1 mg/vial NaCl, and 42.9 mg/vial sodium citrate. The vials are reconstituted with Sterile Water for Injection, USP, to give a concentration of about 2 mg/ml APC, and this diluted APC is then added to 0.9% Sodium Chloride Injection to give a concentration of from about 100 to about 5000 μg/ml APC for administration to a patient. This is a particularly preferred formulation for administration of APC by subcutaneous injection techniques as described under Section B above.

Whether administered topically or by sub cutaneous injection, in certain embodiments, the relevant formulation may contain protein C as an alternative to, or in addition to APC. For instance, an effective amount of protein C can be administered which will be activated in vivo by the endogenous protein C pathway to produce APC. See, e.g., U.S. Pat. No. 5,151,268 and PCT application WO 93/09807. As noted above, protein C can be purified from plasma or can be made by recombinant DNA techniques. See, e.g., U.S. Pat. Nos. 4,959,318, 4,981,952, 5,093,117, 5,151,268, 5,571,786, 6,156,734, 6,268,344, and 6,395,270. Suitable pharmaceutical compositions comprising protein C are known (see, e.g., U.S. Pat. Nos. 5,151,268 and 5,571,786).

Endogenous production of APC can also be increased by administering an amount of an agent that increases the synthesis of protein C in the animal. See, e.g., PCT application WO 93/09807. Suitable agents include anabolic steroids (e.g., danazolol). See, e.g., PCT application WO 93/09807.

In certain embodiments, endogenous production of APC can be increased by administering an amount of a protein C activator effective to cause the production of APC in vivo from endogenously synthesized protein C and/or from co-administered protein C. See, e.g., PCT application WO 93/09807. A protein C activator is any compound that causes or increases the generation of APC. Suitable protein C activators include thrombin, α-thrombin, active site acylated thrombin, thrombin analogs and mutants (e.g., thrombin E192Q and thrombin K52E), soluble thrombin-thrombomodulin complexes, agents that would prevent clearance or decay of thrombin-thrombomodulin complexes, agents that enhance the synthesis or delay the clearance of thrombomodulin, a venom (such as Protac or Russel Viper venom), factor Xa, plasmin, trypsin, and any other venom, enzyme or compound capable of causing or increasing the generation of APC from protein C. See, e.g., PCT application WO 93/09807. Preferred protein C activators are thrombin and active site acylated thrombin.

In some embodiments, APC may be administered with another agent for controlling one or more or inflammation, cell proliferation and apoptosis. One particularly preferred agent is an anti-IL-17 antibody, in particular Ixekizumab, which showed significant improvements in skin disease severity scores compared with placebo in a Phase II Study in Patients With Chronic Plaque Psoriasis (NEJM, 2012). Other examples of agents for controlling inflammation include TNF-α inhibitors and anti-inflammatory cytokines and biopharmaceuticals.

It will be understood that the invention disclosed and defined in this specification extends to all alternative combinations of two or more of the individual features mentioned or evident from the text or drawings. All of these different combinations constitute various alternative aspects of the invention.

Further aspects of the present invention and further embodiments of the aspects described in the preceding paragraphs will become apparent from the following description, given by way of example and with reference to the accompanying drawings.

EXAMPLES

Example 1. Pre-Clinical Trial Establishing the Selective Anti-Apoptotic Activity of APC on Slow Growing, Non Inflammatory Keratinocytes and Psoriasis Skin Keratinocytes Six patients with active chronic plaque psoriasis and 6 normal individuals are recruited. They have not received any treatment for at least 4 weeks prior to sampling. Two 6-mm punch biopsies are taken under local anesthetic from the same chronic plaque. Keratinocytes are isolated as we described previously (20).

Normal keratinocytes are treated with a mixture of cytokines [IL-1a (10 ng/ml), IL-6 (5 ng/ml), TNF-α (5 ng/ml), IL-17A (10 ng/ml)] to induce a psoriatic phenotype. APC is added to keratinocytes at 1, 10 μg/ml and treated for 24, 48 and 72 hrs. Cell proliferation/survival is examined using MTT assay, Brdu proliferation assay. Cell apoptosis is examined by TUNEL assay, Flow cytometry (propidium iodide (PI) or PI plus annexin-V). Cytokine production and four selected psoriasis-associated genes TNF, DEFB4, CAMP, PI3 are detected by RT-real time PCR and ELISA. The activation and expression of apoptotic signal molecules capase-3, 8 and 9 and MAK kinase ERK are detected by western blot.

The results will show that APC induces the apoptosis of, and slows the growth of psoriatic keratinocytes while it stimulates the growth and survival of the normal keratinocytes. APC also reduces the levels of inflammatory cytokines IL-1, TNF-α, IL-17 and IL-6 and psoriasis-associated molecules TNF, DEFB4, CAMP, PI3. In the normal control cells that are treated with inflammatory mediators, cell growth is enhanced and the addition of APC reverses this effect. Overall, the results will clearly show that APC can not only inhibit the inflammation associated with psoriatic keratinocytes, but it also reduces the characteristic excessive proliferation associated with these cells.

Example 2. A Phase 2 Pilot Trial with Subcutaneous APC Over 12 Weeks

Patient selection: 5 Patients with severe chronic plaque-type psoriasis [Psoriasis Area and Severity Index (PASI)≥12, body surface area (BSA)≥10] are enrolled. Primary inclusion criteria includes patients 18 to 70 years of age who have had stable plaque psoriasis for at least 6 months. Primary exclusion criteria includes: i) patients with non-plaque or drug-induced psoriasis; ii) the use of biologicals such as rituximab, abatacept, infliximab, adalimumab, cyclosporine, or mycophenolic acid and etanercept or anakinra within 28 days prior to study iii) patients who have received anti-psoriatic treatment, including any phototherapy, during 8 weeks preceding the study and treatment with any standard topical therapy for psoriasis other than with bland emollients during 4 weeks preceding the study; iv) the use of topical therapy during the study is limited to class III to VII glucocorticoids on the scalp, axillae, and groin only; v) evidence of any active or recent infections, or a history of malignancy or other autoimmune disease, pregnant women are also exclusion criteria.

Treatment: Patients are administered with 400 ug APC/plaque subcutaneously twice a week for up to 12 weeks or when plaques resolve. APC is injected evenly around (as previously described) the periphery and under psoriatic plaques and vehicle alone (placebo) is injected similarly into control plaques symmetrically localized on the other body side. Patients are then followed up for an additional 4 weeks after the final treatment.

Measurement: The PASI, static Physician's Global Assessment (sPGA), Dermatology Life Quality Index (DLQI), adverse events, and routine haematological and laboratory values (e.g. cytokine, histological examination, PC/APC activity) are analysed. Safety considerations include bleeding risk, headache, fatigue, infection and allergy. Relevant cell and biochemistry events include white blood cell, neutrophil, and platelet counts; coagulation activity, PC/APC levels and antibody formation to APC in serum. A 4 mm biopsy is taken to perform histological examination of PC/APC and EPCR, and the evaluation of the main psoriatic parameters such as acanthosis, hyperkeratosis, and parakeratosis, the mitotic activity of the epidermis, papillary edema, dilation and tortuosity of capillaries, and neutrophils in the dermis, the stratum spinosum, as well as in the horny layer, respectively.

Statistical analysis: Baseline values and values at weeks during treatment, and 4 weeks after treatment are compared at a significance level of 0.05, using a 1-sided 2-sample t-test.

Results and Discussion: APC treatment will be shown to be safe and well tolerated and patients will show at least 60% resolution of psoriasis lesions, with 3 of 5 patients showing complete resolution of the plaque. APC's effect shall be sustained during the 4 week follow-up. All patients will show improved PASI, sPGA, DLQI and with no adverse effects and no APC antibodies formed in response to the treatment. Significant reductions in the thickness of epidermis and inflammatory cells in the skin can be observed, and an increase in keratinocyte expression of EPCR, however, circulating PC/APC levels are not affected. Overall, the results will show that APC is safe, well tolerated and highly efficacious for psoriasis plaques.

Example 3 A Phase 2 Pilot Trial with Subcutaneous aPC for Acne Vulgaris in 10 Patients Patient selection: 10 Patients with acne vulgaris are enrolled. Primary inclusion criteria includes: patients 18 to 30 years of age who have had bilateral facial acne for at least 6 months. Primary exclusion criteria includes evidence of any active or recent infections, or a history of malignancy or other autoimmune disease, pregnant women.

Treatment: Patients are administered with 200 ug APC in gel form once a day for 12 weeks or when acne resolves. The patients are provided with two tubes of gel marked L and R and advised to apply 2 cm of gel, squeezed from the tube, to the designated affected area (L on left side of face and R on right side of face) and rub in evenly. Patients are then followed up for an additional 4 weeks after the final treatment.

Measurement: Photographs are taken before treatment and every 4 weeks and acne area calculated using computer-assisted image analysis. Adverse events, and routine haematological and laboratory values (e.g. cytokine, histological examination, PC/APC activity) are analysed. Safety including bleeding risk, headache, fatigue, infection, allergy are monitored. Relevant cell and biochemistry events include white blood cell, neutrophil, and platelet counts; coagulation activity, PC/APC levels and antibody formation to APC in serum.

Statistical analysis: Baseline values and values at weeks during treatment, and 4 weeks after treatment were compared at a significance level of 0.05, using a 1-sided 2-sample t-test.

Results and Discussion: APC treatment will be shown to be safe and well tolerated and patients will show at least 50% resolution of the acne. APC's effect will be sustained during the 4 week follow-up. There will be no adverse effects and no APC antibodies formed in response to the treatment. There should be significant reductions in the thickness of epidermis and inflammatory cells in the skin, an increase in keratinocyte expression of EPCR, however, circulating PC/APC levels are not affected. Overall, our results will show that APC is safe, well tolerated and highly efficacious for acne vulgaris.

Example 4 Gel Formulation and Therapeutic Application

This example offers a non-sterile, low bioburden, preserved, sodium carboxymethylcellulose-based topical gel, containing the active ingredient activated protein C and the following inactive ingredients: carboxymethylcellulose sodium, glacial acetic acid, 1-lysine hydrochloride, m-cresol, methylparaben, propylparaben, sodium acetate trihydrate, sodium chloride, and water for injection. Each gram of Gel contains 100 ug activated protein C.

Example 5 Gel Formulation and Therapeutic Application

Carbopol®*Ultrez 30 polymer (Lubrizol Advanced Materials, Inc) offers good viscosity in combination with xanthan gum in the presence of 1% salicylic acid and 5% of an electrolyte containing extract, in this cold process formulation at pH 4. Glucam™* E 20 humectant, along with glycerin, imparts humectancy. Below is the formula.

|   | INCI Name, Trade Name | Weight % | Function |
|---|---|---|---|
| A. | 1. Deionized Water | 79.15 | Diluent |
|    | 2. Disodium EDTA, Protachem NA2 | 0.05 | Chelating Agent |
|    | 3. Carbomer, Carbopol ®* Ultrez 30 Polymer | 0.80 | Rheology Modifier |
| B. | 4. Glycerin, Glycerin, 99.7% USP | 2.00 | Humectant |
|    | 5. Methyl Gluceth-20, Glucam ™* E-20 Humectant | 1.00 | Humectant |
|    | 6. Xanthan Gum, Keltrol ® CG | 0.25 | Thickener |
| C. | 7. Sodium Hydroxide (18% Solution) | 1.75 | Neutralizer |
| D. | 8. Butylene Glycol | 6.00 | Solubilizer |
|    | 9. Alcohol, Ethyl Alcohol | 2.00 | Solubilizer |
|    | 10. Salicylic Add | 1.00 | Anti-Acne Agent |
| E. | 11. PEG-40 Hydrogenated Castor Oil, Cremophor ® CO-40 | 0.25 | Solubilizer |
|    | 12. Lauryl Lactate, Schercemol ™* LL Ester | 0.25 | Emollient |
| F. | 13. Phenoxyethanol (and) Ethylhexylglycerin, Euxyl ® PE 9010 | 0.50 | Preservative |
|    | 14. Water, Glycerin | 5.00 | Anti-irritant |

Procedure:
1. Combine PART D ingredients and mix until Salicylic Acid Crystals are fully dissolved. Set aside for later addition.

2. Dissolve Disodium EDTA in water. When Disodium EDTA is fully dissolved, set mixing speed @400-500 rpm and slowly disperse Carbopol®* Ultrez 30 polymer into water. continue mixing until polymer is fully hydrated.

3. Premix PART B ingredients into a uniform slurry. Add to PART A. Increase mixing speed as needed to maintain uniformity.

4. Add PART C to PART AB and increase mixing speed as needed to maintain uniformity. Continue mixing for 10 minutes.

5. Add PART D to batch and adjust mixing speed as needed to reduce any splashing due to viscosity change. Mix until uniform.

6. Premix PART E ingredients and add to batch. Mix until uniform.

7. Add PART F ingredients individually with good mixing between additions.

APC is added to an amount of 10-5000 µg/g gel or 0.01-0.05 w/w %

This gel can be applied directly to lesion areas.

Example 6 Spray on Formulations and Therapeutic Applications

APC was solubilised in an isotonic sterile solution as described above for APC by injection. Spray delivery was achieved by drawing up the contents of the vial into a 2.5 ml syringe using a drawing needle. A sterilised spray nozzle was fitted to the end of the syringe (in place of the needle) and the treatment (APC or saline) was evenly sprayed onto the plaque in order to cover the entire affected surface. Thus, no propellant was required to obtain atomisation, merely the pressure applied to the syringe. Application was repeated as necessary, preferably once a day. This technique is easy to perform and repeat in a consistent manner providing an even coverage of treatment.

Example 7 Techniques for Assessment of Anti-Apoptotic Effect on Normal Keratinocytes and Apoptotic Effect on Hyperproliferative Keratinocytes According to the invention, a therapeutically effective amount of APC generally provides an anti-apoptotic effect on normal keratinocytes and an apoptotic effect on hyperproliferative keratinocytes. This outcome can be assessed in vitro or in situ as follows:

In Vitro Method 1.

Untreated active psoriatic skin is removed using a biopsy punch and keratinocytes are isolated. Briefly, cells (3000 cells/well) are seeded in 96 well-plates to a final volume of 200 µl, then incubated for 4 hours to allow cells to attach. Cells are then treated with APC at 0.1, 1 and 10 µg/ml for 72 hrs.

1) Cell survival/growth rate by MTT assay: In this assay, mitochondrial dehydrogenases of viable cells cleave the tetrazolium ring, yielding purple MTT formazan crystals which are insoluble in aqueous solutions. The crystals can be dissolved in acidified isopropanol. The resulting purple solution is spectrophotometrically measured. An increase in cell number results in an increase in the amount of MTT formazan formed and an increase in absorbance. Three hours prior to the completion of the treatment, 10 µl of 5 mg/nil MTT is added to cells. After a further incubation 3 hours, the MTT solution is removed and replaced by 100 µl DMSO. The optical density of each well is determined at a wavelength of 570 nm with a reference wavelength of 630 nm. The viability of cells is directly related to OD. APC reduced the viability in a dose-dependent manner.

2) Apoptotic rate detection was by TUNEL assay, FACS analysis with propidium iodide (PI) or PI plus annexin-V) and active caspase activity.

TUNEL assay is performed using an in situ cell death detection kit according to manufacturer's instructions (Roche Diagnostics Australia Pty. Ltd., NSW, Australia). Briefly, cells are permeabilised with 0.1% Triton X-100 in freshly prepared 0.1% sodium citrate, and incubated with terminal deoxynucleotidyl transferase in the presence of fluorescein-labeled dUTP (60 min at 37° C.). TUNEL positive cells were visualized using an anti-fluorescein peroxidase (POD) conjugated antibody and POD substrate reaction. Sections were counterstained with DAPI. The frequency of apoptotic cells was determined by a blinded investigator by counting TUNEL positive cells and total cell number under a high magnification view (40×) and calculating the percentage of TUNEL positive cells.

FACS analysis: Keratinocytes are trypsinized and washed with FACS washing buffer (PBS with 5% FCS). A 200 µl cell suspension is incubated with propidium iodide (PI) or PI plus annexin-V or conjugated antibodies, and subsequently detected by a flow cytometer for cell cycles/cell apoptosis and protein expression. Data is analyzed using FlowJo software.

Active caspase activity is detected by western blot. Following treatment, keratinocytes are washed three times with PBS and lysis buffer (0.15 M NaCl, 0.01 mM PMSF, 1% NP-40, 0.02 M Tris, 6 M urea/$H_2O$) supplemented with protease inhibitor and phosphate inhibitor (Roche, Indianapolis, Ind., USA) was added. Cell lysates are centrifuged at 10,000 g for 15 minutes and supernatants are separated by 10% sodium-dodecyl-sulphate polyacrylamide-gel electrophoresis (SDS-PAGE) and transferred to a PDVF membrane. Anti-human caspase-3, 8 and 9 antibodies are detected. Immunoreactivity is detected using the ECL detection system (Amersham, Piscataway, N.J.). Anti-human β-actin antibody was included to normalize against unequal loading.

In all apoptosis assays APC promotes apoptosis of fast-growing keratinocytes.

In Vitro Method 2.

The aim is to determine whether keratinocytes from APC-treated plaques are more prone to apoptosis than placebo-treated cells. APC is delivered to psoriatic plaques (~5-50 $cm^2$ in size) using 2 methods: i) topical injection (100 ng-1 mg); ii) spraying a solution (10 ng-1 mg), using sterilised spray nozzle on end of 0.5 ml syringe). Active psoriatic skin treated with either APC or placebo are removed using biopsy punches and keratinocytes are isolated. Cells are immediately measured for apoptosis using FACS analysis, as described above. Results indicated that there are significantly higher levels of apoptotic cells from APC-treated skin, compared to placebo-treated skin.

In Situ Method in situ cell apoptosis: The aim is to determine whether keratinocytes from APC-treated plaques are more prone to apoptosis than placebo-treated cells. APC is delivered to psoriatic plaques (~5-50 sq cm in size) using 2 methods: i) topical injection (100 ng-1 mg); ii) spraying a solution (10 ng-1 mg), using sterilised spray nozzle on end of 0.5 ml syringe). Active psoriatic skin treated with either APC or placebo is removed using biopsy punches. Skin is fixed and cell apoptosis is detected using an in situ cell death detection kit according to manufacturer's instructions (Roche Diagnostics Australia Pty. Ltd., NSW, Australia). Briefly, cells are permeabilised with 0.1% Triton X-100 in freshly prepared 0.1% sodium citrate, and incubated with terminal deoxynucleotidyl transferase in the presence of fluorescein-labeled dUTP (60 min at 37° C.). TUNEL positive cells are visualized using an anti-fluorescein peroxidase (POD) conjugated antibody and POD substrate reaction. Sections are counterstained with DAPI. The frequency of apoptotic cells is determined by a blinded investigator by counting TUNEL positive cells and total cell number under a high magnification view (40×) and calculating the percentage of TUNEL positive cells. Skin treated with APC has significantly higher levels of TUNEL-positive apoptotic cells compared to placebo-treated skin.

Mouse Model of Psoriasis

The psoriasis xenograft SCID mouse model (82 mice required) is performed as previously described (Raychaudhuri, 2001 Br. J. Dermatol). Briefly, human psoriatic plaques (1 cm$^2$) are grafted onto the back of an ~8-week-old SCID mice after removing a full-thickness skin sample. The psoriatic grafts are accepted in 3-4 weeks and the psoriasis-like disease is maintained for at least 10 weeks. APC is delivered after psoriasis development using 2 methods: i) intradermal injection (10 ng-100 ug); ii) spraying a solution (10 ng-100 ug), using a sterilised spray nozzle on the end of 0.5 ml syringe) on affected skin (8/group) 3 times/week for up to 8 weeks. Physiological saline is used as placebo control. Punch biopsies (2 mm), taken on day 0 (before treatment) and day 28 (after treatment), are snap frozen and processed for immunostaining and histology to determine epidermal thickness, rete peg length (an indicator of epidermal thickness) and inflammatory cellular infiltrates. On day 28, skin is collected to measure inflammatory mediators, differentiation markers and junctional proteins. APC treatment reduces the thickness of the skin and the number of inflammatory cells, particularly the neutrophils and T cells. Inflammatory cytokines in APC-treated skin are reduced, particularly tumour necrosis factor-$\alpha$ and junction-associated proteins are increased, especially zona occludens-1 claudins, occludins, and JAM-A, compared to placebo.

Cell proliferation using BrdU incorporation: To achieve labelling of cells undergoing DNA synthesis, adult mice receive one injection of BrdU (100 mg/kg) 2 h before euthanasia, and mouse skins are collected and fixed with 10% formalin. Proliferative cells are detected by immunostaining with anti-BrdU antibody. APC-treated cells exhibit significantly less BrdU incorporation indicating lower proliferative capacity.

Example 8 A Phase 2 Pilot Trial with Subcutaneous APC Over One Month in Five Patients Patients Patients 18 to 70 years of age who had stable plaque psoriasis for at least 6 months, had received or were candidates for phototherapy or systemic psoriasis therapy.

Exclusions:

Patients with non-plaque or drug-induced psoriasis.

Patients who had received anti-psoriatic treatment, including any phototherapy, during 8 weeks preceding the study and treatment with any standard topical therapy for psoriasis other than with bland emollients during 4 wk preceding the study. The use of topical therapy during the study would be limited to class III to VII glucocorticoids on the scalp, axillae, and groin only.

Patients with clinical evidence for infection during 3 weeks before the study, and patients with a history of cancer.

Study Design

A phase 2 pilot trial with subcutaneous APC (100 ug) weekly for one month in five patients.

APC Administration Protocol.

Five otherwise healthy, male patients with chronic plaque psoriasis are chosen for treatment with APC. The drug is administered weekly over a period of 4 weeks in a dosage of 100 ug.

APC is injected subcutaneously directly under psoriatic plaques and vehicle alone (placebo) is injected under a control plaque symmetrically localized on the other body side. A control plaque comparable to the other two is selected for study with neither injection Reporting Descriptive Analysis (Baseline)

The baseline demographic (age, weight, BMI, ethnicity) and disease characteristics (duration of psoriasis, percentage of body area affected by psoriasis, mean PASI score, the presence of marked or severe psoriasis), as assessed by means of the static physician's global assessment, prior topical treatment, prior phototherapy, prior systemic therapy, prior biologic therapy.

Efficacy and Safety Evaluations

Efficacy from day 1 (before therapy) up to 3 d after the end of therapy (day 31) by photo documentation and/or 20 mHz ultrasound.

Three different plaques (including the site of APC and vehicle administration) are monitored in detail in each patient to determine the reduction in the echo-poor band (representing both epidermal acanthosis and the infiltrate in the upper dermis) the percentage improvement in the psoriasis area and severity index (PASI) of each patient.

Skin biopsies (4-mm punch biopsies) 4 day before APC at one week and at day 24 (end of therapy) for histological and immune-histochemical examination as well as mRNA.

Histology and Immunohistochemistry

The histological investigations include the evaluation of the main psoriatic parameters such as acanthosis, hyperkeratosis, and parakeratosis, the mitotic activity of the epidermis, papillary edema, dilation and tortuosity of capillaries, and neutrophils in the dermis, the stratum spinosum, as well as in the horny layer, respectively Immunohistochemical Investigations Safety Adverse events, serious adverse events, Routine hematologic and laboratory values, Antibody formation to APC.

Side-effects and the pruritus

Delayed type of hypersensitivity reaction (DTH)

REFERENCES

1. Chiricozzi, A., Guttman-Yassky, E., Suarez-Farinas, M., Nograles, K. E., Tian, S., Cardinale, L, Chimenti, S., and Krueger, J. G. (2011) J Invest Dermatol 131, 677-687
2. Nestle, F. O., Di Meglio, P., Qin, J. Z., and Nickoloff, B. J. (2009) Nat Rev Immunol 9, 679-691
3. Pasparakis, M. (2009) Nat Rev Immunol 9, 778-788
4. Pasparakis, M. (2012) Immunol Rev 246, 346-358
5. Zanni, G. R. (2012) Consult Pharm 27, 86-88, 90, 93-86
6. Berth-Jones, J., and Hutchinson, P. E. (1992) Br J Dermatol 127, 71-78
7. Kurian, A., and Barankin, B. (2011) Skin Therapy Lett 16, 4-7
8. Tran, B., and Feldman, S. R. (2011) J Dermatolog Treat 22, 18-26
9. Herrier, R. N. (2011) American Journal of Health-System Pharmacy 68, 795-806

10. Montesu, M. A., Addis, G. M., Satta, R., and Cottoni, F. (2011) G Ital Dermatol Venereol 146, 273-281
11. Wallis, R. S. (2011) Infect Dis Clin North Am 25, 895-910
12. Esmon, C. T. (2004) Crit Care Med. 32, S298-S301
13. Xue, M., Campbell, D., and Jackson, C. J. (2007) Journal of Biological Chemistry 282, 13610-13616
14. Xue, M., Campbell, D., Sambrook, P. N., Fukudome, K., and Jackson, C., J. (2005) J Invest Dermatol. 125, 1279-1285
15. Esmon, C. T. (2004) Maturitas 47, 305-314
16. Yuksel, M., Okajima, K., Uchiba, M., Horiuchi, S., and Okabe, H. (2002) Thromb. Haemost. 88, 267-273
17. Xue, M., March, L., Sambrook, P. N., Fukudome, F., and Jackson, C. J. (2007) Ann. Rheum. Dis.
18. Xue, M., March, L., Sambrook, P. N., and Jackson, C. J. (2007) Arthritis Rheum. 56, 2864-2874
19. Lay, A. J., Donahue, D., Tsai, M. J., and Castellino, F. J. (2007) Blood 109, 1984-1991
20. Xue, M., Thompson, P., Kelso, I., and Jackson, C. (2004) Exp Cell Res 299, 119-127
21. van Zonneveld, A. J., de Boer, H. C., van der Veer, E. P., and Rabelink, T. J. (2010) Annals of the Rheumatic Diseases 69, i57-i60
22. Feistritzer, C., and Riewald, M. (2005) Blood 105, 3178-3184
23. Finigan, J. H., Dudek, S. M., Singleton, P. A., Chiang, E. T., Jacobson, J. R., Camp, S. M., Ye, S. Q., and Garcia, J. G. (2005) J. Biol. Chem.
24. Xue, M., Chow, S. O., Dervish, S., Chan, Y. K., Julovi, S. M., and Jackson, C. J. (2011) Journal of Biological Chemistry 286, 6742-6750
25. Vetrano, S., Ploplis, V. A., Sala, E., Sandoval-Cooper, M., Donahue, D. L., Correale, C., Arena, V., Spinelli, A., Repici, A., Malesci, A., Castellino, F. J., and Danese, S. (2011) Proc Natl Acad Sci USA 108, 19830-19835
26. Uchiba, M., Okajima, K., Oike, Y., Ito, Y., Fukudome, K., Isobe, H., and Suda, T. (2004) Circ Res 95, 34-41

The invention claimed is:

1. A method of inducing apoptosis of hyperproliferative keratinocytes in an individual having a skin disorder characterized by the presence of hyperproliferative keratinocytes, the skin disorder selected from the group consisting of acne, dermatitis herpetiformis, and atopic dermatitis, wherein the method comprises:
contacting a region of skin of the individual that is characterized by acne, dermatitis herpetiformis, or atopic dermatitis with a therapeutically effective amount of activated protein C (APC),
thereby inducing apoptosis of hyperproliferative keratinocytes in the region of the skin characterized by acne, dermatitis herpetiformis, or atopic dermatitis.

2. The method of claim 1, wherein the therapeutically effective amount of APC decreases inflammation in the region of skin.

3. The method of claim 1, wherein the therapeutically effective amount of APC inhibits apoptosis of slow growing/normal keratinocytes in the region of skin.

4. The method of claim 1, wherein the therapeutically effective amount of APC does not inhibit the growth of normal keratinocytes, or induce proliferation of normal keratinocytes.

5. The method of claim 1, wherein the therapeutically effective amount of APC is from 1 µg to 5 mg of APC per $cm^2$ of the region of skin.

6. The method of claim 1, wherein the APC is provided in the form of a gel, cream, ointment, spray, or lotion adapted for contact with the skin surface.

7. The method of claim 1, wherein the APC is provided for contact with the region of skin in the form of a composition adapted for subcutaneous injection.

8. The method of claim 1, wherein the skin disorder is further characterized by one or more of the following processes: apoptosis, inflammation and impaired barrier function.

9. The method of claim 1, wherein the method further includes administration of an additional anti-inflammatory agent in the individual.

10. The method of claim 1, wherein the skin disorder characterized by the presence of hyperproliferative keratinocytes is dermatitis herpetiformis.

11. The method of claim 1, wherein the skin disorder characterized by the presence of hyperproliferative keratinocytes is acne.

12. The method of claim 1, wherein the skin disorder characterized by the presence of hyperproliferative keratinocytes is atopic dermatitis.

13. The method of claim 2, wherein the method further includes administration of an additional anti-inflammatory agent in the individual.

14. The method of claim 3, wherein the method further includes administration of an additional anti-inflammatory agent in the individual.

15. The method of claim 4, wherein the method further includes administration of an additional anti-inflammatory agent in the individual.

16. The method of claim 5, wherein the method further includes administration of an additional anti-inflammatory agent in the individual.

17. The method of claim 6, wherein the method further includes administration of an additional anti-inflammatory agent in the individual.

18. The method of claim 7, wherein the method further includes administration of an additional anti-inflammatory agent in the individual.

19. The method of claim 8, wherein the method further includes administration of an additional anti-inflammatory agent in the individual.

20. The method of claim 1, wherein inducing apoptosis of the hyperproliferative keratinocytes in the region of the skin characterized by acne, dermatitis herpetiformis, or atopic dermatitis treats the skin disorder.

21. The method of claim 20, wherein treating the skin disorder decreases or eliminates the skin disorder.

* * * * *

UNITED STATES PATENT AND TRADEMARK OFFICE
CERTIFICATE OF CORRECTION

PATENT NO. : 11,617,785 B2
APPLICATION NO. : 16/880243
DATED : April 4, 2023
INVENTOR(S) : Jackson et al.

It is certified that error appears in the above-identified patent and that said Letters Patent is hereby corrected as shown below:

On the Title Page

(56) References Cited, OTHER PUBLICATIONS, Page 2, Column 2, Line 42: Please correct "Bettinger et ai." to read --Bettinger et al.--

(56) References Cited, OTHER PUBLICATIONS, Page 3, Column 2, Line 62: Please correct "WANG et ai." to read --WANG et al.--

(56) References Cited, OTHER PUBLICATIONS, Page 4, Column 1, Line 18: Please correct "Protein 0" to read --Protein C--

(56) References Cited, OTHER PUBLICATIONS, Page 4, Column 2, Line 9: Please correct "Factor-a" to read --Factor-α--

In the Specification

Column 11, Line 25: Please correct "PAST" to read --PASI--

Column 14, Line 16: Please correct "IL-1a" to read --IL-1α--

Column 17, Line 8: Please correct "PART AB" to read --PART A/B--

Signed and Sealed this
Sixteenth Day of April, 2024

Katherine Kelly Vidal
*Director of the United States Patent and Trademark Office*